(12) United States Patent
Sato

(10) Patent No.: US 7,591,100 B2
(45) Date of Patent: Sep. 22, 2009

(54) METHOD OF PRODUCING SEED AND PLANT CONTAINING VITAMIN $B_{12}$

(75) Inventor: Kazuyoshi Sato, Hiroshima (JP)

(73) Assignee: Hiroshima University, Higashi-Hiroshima (JP)

( * ) Notice: Subject to any disclaimer, the term of this patent is extended or adjusted under 35 U.S.C. 154(b) by 236 days.

(21) Appl. No.: 10/456,899

(22) Filed: Jun. 9, 2003

(65) Prior Publication Data

US 2003/0233673 A1    Dec. 18, 2003

(51) Int. Cl.
| | | |
|---|---|---|
| A01C 1/00 | (2006.01) |
| A01G 7/00 | (2006.01) |
| A01H 4/00 | (2006.01) |
| A01G 31/00 | (2006.01) |
| A23L 1/30 | (2006.01) |
| A01C 1/06 | (2006.01) |
| A01C 21/00 | (2006.01) |
| A01G 17/08 | (2006.01) |
| A01G 9/08 | (2006.01) |

(52) U.S. Cl. .................. 47/58.1 SE; 47/61; 47/57.6; 47/1.01; 426/72; 111/918

(58) Field of Classification Search .................. None
See application file for complete search history.

(56) References Cited

U.S. PATENT DOCUMENTS

| 5,773,681 A | 6/1998 | Fuchs |
| 6,309,440 B1 | 10/2001 | Yamashita |

FOREIGN PATENT DOCUMENTS

| CA | 1 337 244 | 10/1995 |
| CN | 1273022 A | 11/2000 |
| GB | 1 108 164 | 4/1968 |
| JP | 60-36402 | 8/1985 |
| JP | 1-240173 | 9/1989 |
| JP | 3-5409 | 1/1991 |
| JP | 2001-10 | 1/2001 |
| WO | WO 01/22822 | 4/2001 |

OTHER PUBLICATIONS

Riley John M. http://www.crfg.org/tidbits/seedprop.html 1997.*
Attwood Charles Vitamin B-12 http://www.vegsource.com/attwood/vitB-12.htm.*
Sprout Production Commercial Vegetable Production Guides http://oregonstate.edu/Dept/NWREC/beansprt.html 2002, Apr. 2002.*
Yoshida, et al., Agriculture and Horticulture, vol. 73, No. 8., pp. 61-67, "Analysis of Production of Vitamin $B_{12}$.—Enriched Vegetables", 1998 (with partial English translation).
A. Mozafar, Vegetarian Nutrition: An International Journal, pp. 50-52, "Is There Vitamin $B_{12}$ in Plants or Not? A Plant Nutritionist's View", 1997.
A. Mozafar, et al., Plant and Soil, vol. 139, pp. 23-30, "Uptake of a Microbially-Produced Vitamin (B12) by Soybean Roots", 1992.
P. Mattila, et al., J. Agric. Food Chem., vol. 49, pp. 2343-2348, XP-002259127, "Contents of Vitamins, Mineral Elements, and Some Phenolic Compounds in Cultivated Mushrooms", 2001.
Lintschinger, J., et al., "Selenium-Enriched Sprouts. A Raw Material for Fortified Cereal-Based Diets," J. Agric. Food Chem., vol. 48, 2000, pp. 5362-5368.
Bewley, J. D., "Seed Germination and Reserve Moblization," Encylopedia of Life Science, 2001, pp. 1-7.
Definition of Seedling, Wikipedia, (2 pages).
P. Mattila, et al., J. Agric. Food Chem, vol. 49, pp. 2343-2348, XP-002259127, "Contents of Vitamins, Mineral Elements, and Some Phenolic Compounds in Cultivated Mushrooms", 2001.

* cited by examiner

Primary Examiner—Annette H Para
(74) Attorney, Agent, or Firm—Oblon, Spivak, McClelland, Maier & Neustadt, L.L.P.

(57) ABSTRACT

The present invention is directed to producing a plant containing vitamin $B_{12}$. Accordingly, the present invention provides a seed and a plant containing vitamin $B_{12}$. The present invention is also directed to a method of producing a plant containing vitamin $B_{12}$ comprising soaking a seed, spore or hypha of a plant in a soaking solution containing vitamin $B_{12}$, and cultivating the seed, spore or hypha of the plant thus soaked. Furthermore, the present invention provides a soaking solution containing vitamin $B_{12}$ for introducing vitamin $B_{12}$ into a plant.

6 Claims, 1 Drawing Sheet

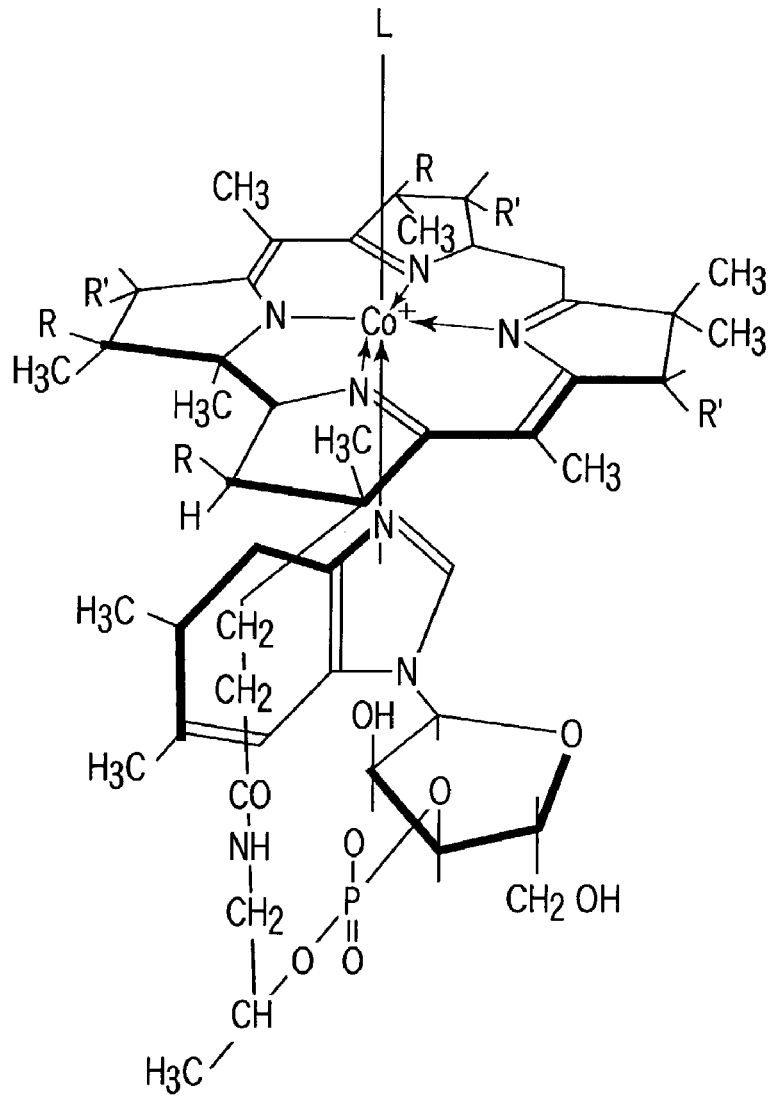
FIGURE

METHOD OF PRODUCING SEED AND PLANT CONTAINING VITAMIN $B_{12}$

CROSS-REFERENCE TO RELATED APPLICATIONS

This application is based upon and claims the benefit of priority from prior Japanese Patent Applications No. 2002-171323, filed Jun. 12, 2002; and No. 2003-118323, filed Apr. 23, 2003, the entire contents of both of which are incorporated herein by reference.

BACKGROUND OF THE INVENTION

1. Field of the Invention

The present invention relates to a plant containing vitamin $B_{12}$ and a method of producing a plant containing vitamin $B_{12}$.

2. Description of the Related Art

Vitamin $B_{12}$ is an essential vitamin required for maintaining human health. Vitamin $B_{12}$ is required in as small an amount as 2.4 µg per adult per day whereas most of the other essential vitamins and minerals are required in an amount of several mg or more per day. It is known that the deficiency of vitamin $B_{12}$ causes diseases including malignant anemia. Recently, further study is underway on vitamin $B_{12}$ and the responsibility of vitamin $B_{12}$ for causing arteriosclerosis, Alzheimer's disease, and delayed sleep syndrome has been elucidated.

At present, it is known that the most important role of vitamin $B_{12}$ in humans is to participate in the $C_1$ metabolism of a vitamin $B_{12}$-dependent methionine synthase system. Vitamins other than vitamin $B_{12}$, such as folic acid and vitamin $B_6$ are also involved in the $C_1$ metabolism. These vitamins play a role in functioning cells normally by methylating principally amino acids (e.g. homocysteine), nucleic acids, and physiologically active substances. When the normal metabolism is impaired, disorders such as megaloblastic anemia, arteriosclerosis, and neuropathy may be induced.

Vitamin $B_{12}$ is water soluble and relatively tolerable to heat, so that it will not be vaporized or destroyed so much during cooking. When vitamin $B_{12}$ is taken as food into a human body, it is modified with an intrinsic factor of glycoprotein secreted into gastric juice and the vitamin $B_{12}$ bound to the intrinsic factor is absorbed through the small intestine. Because of this, persons whose stomach has been surgically removed suffer from a disease caused by a deficiency of vitamin $B_{12}$, in some cases. Vitamin $B_{12}$ is therefore parenterally administrated to the person after surgery.

On the other hand, since the ability of people to absorb vitamin $B_{12}$ decreases with age, old people are chronically deficient in vitamin $B_{12}$. Also, a vitamin $B_{12}$ deficiency sometimes appears in enthusiastic vegetarians. In this case, oral administration of vitamin $B_{12}$ effectively works.

Vitamin $B_{12}$ is produced only by limited types of vitamin $B_{12}$-producing bacteria. Since animals usually take bacteriologically produced vitamin $B_{12}$, a large amount of vitamin $B_{12}$ is contained in the body. Naturally, animal food such as liver, egg, and seafood becomes to contain a large amount of vitamin $B_{12}$. In contrast, the content of vitamin $B_{12}$ in vegetable food is negligibly small except for seaweeds. Since vitamin $B_{12}$-producing bacteria may be attached to seaweeds such as laver, it is conceivable that vitamin $B_{12}$ is contained in seaweeds.

To maintain health, people usually take vegetable rich in vitamin and mineral, including beans and fruits, in various forms. To prevent unbalanced nutrition caused by busy life of people in the modern society, a wide variety of multivitamin pills and drinks are marketed as supplemental agents for supplying essential nutrients. However, it is preferable that various kinds of nutrients are taken simultaneously in the form of natural food. It follows that food enriched with vitamins and minerals has been demanded.

Vegetables basically contain rich vitamin and mineral. Since vegetables can supply various types of vitamins together, they are considered as excellent natural food. The Ministry of Health, Labor and Welfare recommends, in the promotion movement titled "Healthy Japan 21", that not less than 350 g of vegetable food and not less than 120 g of dark green and dark yellow vegetable/day per adult should be taken. However, even if a large amount of vegetable is daily taken, vitamin $B_{12}$ is still insufficient since general vegetables rarely contain vitamin $B_{12}$.

Therefore, it is desired that not only healthy people but also people described below take a health-food plant containing a sufficient amount of vitamin $B_{12}$ (1) People not fond of animal food
(2) People allergic to animal food
(3) Busy people who do not have time to take well-balanced food
(4) old people whose teeth are too weak to take meat daily
(5) Vegetarians
(6) People who have a stomach problem due to ulcer
(7) People who are not willing to take vitamin in the form of pills.

It is considered that these people are always short of vitamin $B_{12}$ and sometimes lacking in vitamin $B_{12}$. Since vitamin $B_{12}$ is indispensable for maintaining human health, it is significantly important to provide vitamin $B_{12}$ in easy-to-take form.

Prior Art

To make up for the shortage of vitamin, there is an idea that a plant enriched with vitamins and minerals is grown and processed into health food. More specifically, such an idea has been directed to water-soluble vitamins and minerals originally contained in a plant. However, vitamin $B_{12}$ is not originally contained in a plant but biologically synthesized by bacteria. Furthermore, no one has considered that vitamin $B_{12}$ is taken from cultivated plant itself. For this reason, people not fond of animal food take vitamin $B_{12}$ as a medicine by taking a multivitamin pill.

Taking vitamin supplement is one of the means for preventing vitamin deficiency. However, there are some people who does not like taking pills. In view of taking well-balanced nutrition, it is desirable to take vitamin $B_{12}$ from a natural source such as a cultivated plant. Unfortunately, a plant containing a sufficient amount of vitamin $B_{12}$ has not yet been cultivated up to present.

In the case of a large-size vegetable, which takes a long time to grow up, vitamin $B_{12}$ may be sprayed directly to a plant or injected into the soil in order to introduce vitamin $B_{12}$ to the plant. However, since vitamin $B_{12}$ is used in a diluted form in these methods, the content per unit weight will not be improved. In addition, since vitamin $B_{12}$ is expensive, it is desirable that vitamin $B_{12}$ will be introduced into a plant by an inexpensive method consuming a small amount of vitamin $B_{12}$.

In these circumstances, it seems to be really useful to develop a novel means which allows to take vitamin $B_{12}$ (2.4 µg/day per adult) easily at least from a plant through daily meals by introducing a large amount of vitamin $B_{12}$ into a plant originally containing no vitamin $B_{12}$.

Conventional methods of introducing vitamin $B_{12}$ into a plant are described in the following publications.

1. Jpn. Pat. Appln. KOKOKU Publication No. 61-56209

This invention is directed to a plant growth-controlling agent containing vitamin $B_{12}$ as an active ingredient. The publication describes that the active ingredient, vitamin $B_{12}$, has an extremely distinguishable plant growth-controlling activity, which includes a fruit-bearing promoting activity, fruit-drop preventing activity, fruit-growth promoting activity, and an activity of preventing production of rusty fruits. If vitamin $B_{12}$ is applied to fruits such as citrus fruits (e.g. oranges) and grapes, and fruit vegetables such as berries, eggplants, and cucumbers, the period until harvest can be significantly reduced and the yield (number of fruits) and the quality of the fruits can be improved. The present invention is similar to the invention of this document in that vitamin $B_{12}$ is used but differs in method, time, and purpose of using vitamin $B_{12}$.

2. Jpn. Pat. Appln. KOKOKU Publication No. 60-36402

This invention relates to a method of reducing an acid component, more specifically, a method of reducing acid, thereby increasing sugar of a fruit. In other words, the present invention is directed to reducing a sour taste by administering a solution containing B-series vitamins to fruit trees or fruit vegetable. In the method, a single vitamin B or a mixture of at least two vitamins of the B series is dissolved in a small amount of water or solvent, and then the resultant solution is either sprayed onto the surfaces of leaves of a fruit tree or a fruit vegetable or injected into the soil. In this way, a sour taste can be reduced and thereby a sweet taste increases. The present invention is similar to the invention disclosed in the document in that vitamin $B_{12}$ is used but differs in method, time and purpose of using vitamin $B_{12}$.

3. Jpn. Pat. Appln. KOKAI Publication No. 03-5409

The invention relates to an agent for accelerating the differentiation of a flower bud by use of the interaction between cytokinin, gibberellin, nucleic acid, and at least one of vitamins. The differentiation of a flower bud is accelerated by spraying vitamin $B_{12}$ and thereby shortening the period up to the harvest.

The present invention is similar to the invention disclosed in the document in that vitamin $B_{12}$ is used but differs in method, time and purpose of using vitamin $B_{12}$.

BRIEF SUMMARY OF THE INVENTION

According to one aspect of the present invention, there is provided a plant and seed containing vitamin $B_{12}$. According to another aspect of the present invention, there is provided a method of producing a plant containing vitamin $B_{12}$.

The present inventors have conducted intensive studies with the view toward solving the aforementioned problems. As a result, they succeeded in introducing a large amount of vitamin $B_{12}$ into a plant and accomplished the present invention.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawing, which is incorporated in and constitute a part of the specification, illustrate presently preferred embodiments of the invention, and together with the general description given above and the detailed description of the preferred embodiments given below, serve to explain the principles of the invention.

The single FIGURE shows a chemical formula of vitamin $B_{12}$ and derivatives thereof.

DETAILED DESCRIPTION OF THE INVENTION

Now, embodiments of the present invention will be described.

According to one aspect of the present invention, there is provided a plant grown from a seed, spore or hypha containing vitamin $B_{12}$, and the seed, spore or hypha.

As used herein, the vitamin $B_{12}$ refers to cobalamin and a derivative thereof. Any derivative may be used as long as it has the same physiological activity as that of the cobalamin, which is a complete-form vitamin $B_{12}$. Examples of cobalamin and derivatives thereof include, but not limited to, cyanocobaslamin, hydroxocobalamin, methylcobalamin, and adenosylcobalamin. Preferably used is cobalamin, which is a complete-form vitamin $B_{12}$, represented by the chemical formula shown in the FIGURE. Usually, CN—$B_{12}$ (cyanocobalamin) may be used as the vitamin $B_{12}$ of the present invention. As used herein, the vitamin $B_{12}$ will be sometimes simply expressed as "$B_{12}$".

As used herein, examples of the plant may include plants belonging to dicotyledon, monocotyledon, and fungi. In other words, the plant of the present invention may be a plant grown from a seed, spore, or hypha.

For example, the plant of the present invention may be cultivated in a short period. Example of such a plant include, but not limited to, plants grown from seeds such as white radish (kaiware daikon) sprouts and bean sprouts, and plants grown from a spore or hypha, such as enoki mushroom and nameko mushroom.

Now, white radish sprouts will be explained as an example of the plant of the present invention. White radish sprouts contain not less than 0.05 µg of vitamin $B_{12}$ per sprout (about 0.1 g). Therefore, the requisite amount of vitamin $B_{12}$ per day (2.4 µg/day/adult) can be taken by eating several tens of sprouts per day. The daily dose of vitamin $B_{12}$ can be satisfied if several sprouts are taken as long as the vitamin $B_{12}$ content of the sprouts has been increased. White radish sprouts may be eaten fresh as well as cooked in any manner.

Vitamin $B_{12}$ is an essential nutrition in a daily life. Vitamin $B_{12}$ can be easily taken if it is contained in food having a good taste and texture. For example, by introducing soybeans, after vitamin $B_{12}$ is introduced therein by the method of the present invention, on the market, a wide variety of processed foods having good taste and texture can be produced.

The processed foods used herein refer to those for humans and animal feed processed by adding the plant of the present invention as a main ingredient or an additive.

Vitamin $B_{12}$ is relatively tolerable to heat. Therefore vitamin $B_{12}$ does not run out from the raw-material plant for processed food during processing. Therefore, the resultant food successfully contains vitamin $B_{12}$ derived from the raw-material plant for processed food. Therefore, the processed foods obtained from the vitamin $B_{12}$-containing plant fall in the range of the present invention. The processed food used herein is not a plant itself but a food product obtained from the plant through cooking or fermentation.

Soybeans may be mentioned as the plant for processed foods satisfying the aforementioned conditions. As an example of the processed food prepared from soybeans, fermented soybeans is mentioned. The soybeans of the present invention (about 0.5 g by dry weight per bean) contain vitamin $B_{12}$ in an amount of not less than 1 µg per edible portion (g) of the soybean seeds. Therefore, a requisite amount of vitamin $B_{12}$ per day (2.4 μg/day per adult) can be easily taken from the soybeans.

Vitamin $B_{12}$ in the form of a chemical agent may be added to a processed food during processing to produce a food product containing vitamin $B_{12}$. Such a processed food falls within the range of conventional techniques and thus outside the range of the technical idea of the present invention.

Any method may be employed to produce raw material soybeans containing vitamin $B_{12}$ according to the embodiment of the present invention. For example, vitamin $B_{12}$ may be absorbed into soybean seeds and immediately subjected to processing. More specifically, vitamin $B_{12}$ may be introduced into soybean seeds by soaking the soybean seeds in a solution containing vitamin $B_{12}$, before scattering over a farmland. However, the efficiency of vitamin $B_{12}$ taken from the plant obtained by introducing vitamin $B_{12}$ into seeds and cultivating them in the soil for a long time, may not be high as compared to that taken from a small plant containing vitamin $B_{12}$, in consideration of vitamin $B_{12}$ as a chemical agent. However, when the processed food prepared by adding a vitamin $B_{12}$ additive in the manufacturing process (in a factory) is compared to that prepared from a vitamin-$B_{12}$ containing raw material, the latter processed food is excellent in safety in most cases. For this reason, the plant of the present invention is an industrially applicable product.

The plant of the present invention is also efficiently used as a raw material for vegetable juice. Commercially available juice prepared by a conventional technique does not contain vitamin $B_{12}$. Juice is a convenient product to take vitamin $B_{12}$. The commercial value of juice can be improved if vitamin $B_{12}$ is introduced into the raw-material plant for process food.

The present invention is concerned with an edible plant, as mentioned above. The plant of the present invention may be used, as other than the edible plant for a human, as a feed plant for animals, such as animals not having the stomach like a lumen, fishes, birds, insects, and reptiles.

The seed, spore or hypha of the present invention can be produced by the following method. The method of producing a plant containing vitamin $B_{12}$ according to the present invention comprises:

soaking a seed, spore, or hypha in a soaking solution containing vitamin $B_{12}$; and cultivating the seed, spore or hypha thus soaked.

A plant satisfying the aforementioned conditions may be used as the plant of the present invention. The period of time for soaking a seed, spore, or hypha may not be particularly limited as long as the time allows the seed or the like to absorb vitamin $B_{12}$. For example, one hour, two hour or not shorter than 5 hours are employed. It is desirable that white radish sprouts may be soaked for 30 minutes, one hour, or not shorter than 3 hours.

The soaking solution of the present invention is one containing vitamin $B_{12}$ in an amount of 0.01 μg/mL, 0.1 μg/mL or 100 μg/mL or more. Since vitamin $B_{12}$ is an extremely high solubility in water, it can be dissolved even in a small amount of water to accomplish a concentration of 10 mg/mL. However, extremely high concentration of vitamin $B_{12}$ of the soaking solution is not preferable since vitamin $B_{12}$ cannot be efficiently absorbed by seeds. Therefore, the preferable concentration of vitamin $B_{12}$ of the soaking solution is about 100 μg/mL. Such a solution may be prepared by dissolving 100 mg of vitamin $B_{12}$ (first-grade reagent) in 1 L of sterilized water.

The concentration of vitamin $B_{12}$ may be varied depending upon the type of plant and cultivation method. More specifically, the concentration of vitamin $B_{12}$ may be 0.1 μg/mL, 1 μg/mL or 10 μg/mL.

After stirring, the resultant mixed solution may be dispensed into transparent or nontransparent containers, stored at low temperature.

An element(s) other than vitamin $B_{12}$ may be contained in the soaking solution, as long as the element(s) will not negatively affect the cultivation of a plant. The method of introducing vitamin $B_{12}$ into a plant according to the present invention is also effectively used in introducing other vitamins and minerals to a plant. Therefore, vitamin $B_{12}$ may be introduced to a plant in combination with desirable element (s). A plant containing vitamin $B_{12}$ and folic acid or iron ions can be produced by preparing a soaking solution containing vitamin $B_{12}$ and folic acid or iron ions in high concentrations.

The seed, spore, or hypha containing vitamin $B_{12}$ can be easily prepared in the aforementioned method.

After they are soaked in the soaking solution, they are grown under suitable cultivation conditions. In this manner, the plant of the present invention can be produced. For example, when white radish sprouts are grown at home, the seeds are soaked at normal temperature in a soaking solution for 3 hours or more and subjected to hydroponics in a plate on which fibers are placed.

Now, the method of cultivating a plant according to the present invention will be described below.

1. Seeds of a plant to be subjected to hydroponics are soaked in a soaking solution of the present invention for 5 hours or more, followed by cultivating the seeds in a general manner to obtain the plant of the present invention.

Although vitamin $B_{12}$ of the soaking solution is absorbed by the seed, the remaining vitamin $B_{12}$ (a considerable amount of vitamin $B_{12}$ is presumably left) may be recycled, if necessary. When vitamin $B_{12}$ is recycled, vitamin $B_{12}$ is treated with heat by means of e.g., microwave, and fresh vitamin $B_{12}$ is added, if necessary, and then subjected to recycle use. In this manner, expensive vitamin $B_{12}$ can be efficiently introduced into a plant without waste.

2. After the seeds are impregnated with vitamin $B_{12}$ they are cultivated on a hydroponic seedbed. Alternatively, seeds (before subjecting to hydroponics) are impregnated with vitamin $B_{12}$ in the same manner as the aforementioned step 1 and then scatted over the soil to allow the seeds to germinate and grow.

The plants grown from spores or hyphae are treated basically in the same manner as those grown from the seeds. More specifically, spores or hyphae of enoki mushroom and nametake mushroom are soaked in a vitamin $B_{12}$-containing soaking solution for a short time and grown under suitable conditions. In this manner, vitamin $B_{12}$ can be introduced into the mushrooms.

In the case of hydroponics, a plant is cultured in a culture solution. In this case, if a small amount of vitamin $B_{12}$ is added to the culture solution, vitamin $B_{12}$ can be absorbed into the growing plant through the root. In this manner, the plant of the present invention can be cropped. Therefore, the plant of the present invention may be cultivated in a culture solution to which the soaking solution of the present invention is previously added.

In the hydroponics, instead of growing a plant after seeds are soaked in a soaking solution containing vitamin $B_{12}$, the plant of the present invention may be produced by a method in which seeds are first germinated and grown in a hydroponic solution containing no vitamin $B_{12}$ and then grown in a hydroponic solution containing vitamin $B_{12}$ to harvest the plant of the present invention.

For example, vitamin $B_{12}$ may be added to a hydroponic solution before 6 hours, 12 hours, one day, 2 days, 3 days or more of the harvest. The amount of vitamin $B_{12}$ contained in the hydroponic solution is preferably 0.1 μg/mL, 1 μg/mL, 10 μg/mL or, 100 μg/mL or more.

Vitamin $B_{12}$ is successfully contained in a plant by the aforementioned method using a small amount of vitamin $B_{12}$.

The method of introducing vitamin $B_{12}$ into a plant according to the present invention will be explained with reference to Example below.

EXAMPLE (Cultivation of White Radish (Kaiware Daikon) Sprouts)

White radish sprout's seeds (1 g) were soaked in a soaking solution containing 200 μg/mL of vitamin $B_{12}$ at room temperature for 6 hours. As a comparative example, white radish sprout's seeds (1 g) were soaked in a soaking solution containing no vitamin $B_{12}$ for 6 hours under the same conditions. Both seeds were scattered on cotton wool, which was moistened with deionized water and placed in 500 mL of beaker in the absence of vitamin $B_{12}$, and allowed to grow for 6 days. When the white radish sprouts grew and reached the length of 6 cm, about 5 g by wet-weight (corresponding to about 50 sprouts) of white radish sprouts was harvested, washed gently with water, and analyzed. Vitamin $B_{12}$ was analyzed by biological quantification using *Lactobacillus delbrueckii* subsp. *lactis* ATCC7830. The samples to be analyzed was prepared as follows. First, white radish sprouts were homogenized with 10 mL of distilled water. To the resultant homogenate, 30 mL of 0.2M acetic acid buffer containing 0.1 mg of KCN was added and heating at 100° C. for 20 minutes, and then, centrifugally separated. The supernatant was appropriately diluted to prepare the specimen for the analysis. Table 1 shows analytical results, that is, the amount (μg/100 g) of vitamin $B_{12}$ contained in 100 g of white radish sprouts. Conditions with respect to a plant, vitamin $B_{12}$ concentration, soaking time, and cultivation method are not limited to those mentioned above. Vitamin $B_{12}$ was introduced into a plant under various conditions (data are not shown).

TABLE 1

Vitamin $B_{12}$ concentration of white radish sprouts

| Material | $B_{12}$ content (μg/100 g) |
| --- | --- |
| $B_{12}$-introduced white radish sprouts | 50.0 |
| No $B_{12}$-introduced white radish sprouts | 0.0 |
| Commercial white radish sprouts | 0.0 |

From the table, it is clear that the white radish sprouts of the present invention contain not less than 0.5 μg/g of vitamin $B_{12}$. The content value corresponds to that of the bovine liver, vitamin $B_{12}$ content of which is regarded highest in animal foods. The content of vitamin $B_{12}$ can be further improved by setting the conditions appropriately. No difference was observed between $B_{12}$-introduced white radish sprout and control in appearance and taste.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of producing edible sprouts containing not less than 0.01 μg of vitamin $B_{12}$ per edible portion (g), said method comprising:
    soaking a seed of the edible sprouts in a soaking solution containing not less than 100 μg/mL of vitamin $B_{12}$;
    removing the seed from the soaking solution and cultivating the seed in a hydroponic seedbed containing no vitamin $B_{12}$; and
    harvesting the edible sprouts containing not less 0.01 μg of vitamin $B_{12}$ per 1 g of the edible portion of the edible sprouts,
    wherein the edible sprouts are white radish (kaiware daikon) sprouts or bean sprouts.

2. The method of producing edible sprouts containing vitamin $B_{12}$ according to claim 1, wherein the edible sprouts are white radish (kaiware daikon) sprouts.

3. A method of producing edible sprouts, comprising:
    soaking a seed of the edible sprouts in a soaking solution containing 100 μg/mL to 200 μg/mL of vitamin $B_{12}$ for 30 minutes to 3 hours;
    removing the seed from the soaking solution and cultivating the seed in a hydroponic seedbed containing no vitamin $B_{12}$; and
    harvesting the edible sprouts containing not less than 0.01 μg of vitamin $B_{12}$ per 1 g of the edible portion of the edible sprouts.

4. The method of producing edible sprouts containing vitamin $B_{12}$ according to claim 3, wherein the edible sprouts are white radish (kaiware daikon) sprouts.

5. The method of producing edible sprouts containing vitamin $B_{12}$ according to claim 3, wherein the edible sprouts are bean sprouts.

6. The method of producing edible sprouts containing vitamin $B_{12}$ according to claim 1, wherein the edible sprouts are bean sprouts.

* * * * *

UNITED STATES PATENT AND TRADEMARK OFFICE
CERTIFICATE OF CORRECTION

| | |
|---|---|
| PATENT NO. | : 7,591,100 B2 |
| APPLICATION NO. | : 10/456899 |
| DATED | : September 22, 2009 |
| INVENTOR(S) | : Sato |

It is certified that error appears in the above-identified patent and that said Letters Patent is hereby corrected as shown below:

On the title page, Item (30), The Foreign Application Priority Data has been omitted. Item (30) should read:

-- (30)     Foreign Application Priority Data

June 12, 2002  (JP)..................................... 2002-171323
April 23, 2003  (JP)..................................... 2003-118323 --

Signed and Sealed this

First Day of June, 2010

David J. Kappos
*Director of the United States Patent and Trademark Office*